US006790443B2

(12) United States Patent
Stern et al.

(10) Patent No.: US 6,790,443 B2
(45) Date of Patent: *Sep. 14, 2004

(54) METHOD FOR TREATING SYMPTOMS OF DIABETES

(75) Inventors: David M. Stern, Great Neck, NY (US); Ann Marie Schmidt, Franklin Lakes, NJ (US)

(73) Assignee: The Trustees of Columbia University in the City of New York, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 40 days.

(21) Appl. No.: 08/755,235

(22) Filed: Nov. 22, 1996

(65) Prior Publication Data

US 2003/0059423 A1 Mar. 27, 2003

(51) Int. Cl.[7] ...................... A61K 39/395; A61K 39/00; A61K 39/38; A61K 47/00
(52) U.S. Cl. .............................. 424/130.1; 424/130.1; 424/158.1; 424/184.1; 424/278.1; 435/325; 435/334; 435/440; 514/2; 530/350; 530/388.22
(58) Field of Search .......................... 424/130.1, 158.1, 424/143.1, 184.1, 278.1; 514/2; 530/350, 388.22; 435/325, 440, 334

(56) References Cited

U.S. PATENT DOCUMENTS

| 4,975,421 A | * | 12/1990 | Williams et al. ............... 514/54 |
| 5,165,938 A | * | 11/1992 | Knighton .................... 424/532 |
| 5,436,228 A | * | 7/1995 | Postlethwaite et al. ....... 514/12 |
| 5,532,275 A | * | 7/1996 | Grumet ...................... 514/567 |
| 5,561,107 A | * | 10/1996 | Jaynes et al. .................. 514/12 |
| 5,561,110 A | * | 10/1996 | Michaelis et al. ............ 514/13 |
| 5,585,344 A | * | 12/1996 | Vlassara et al. | |
| 5,864,018 A | | 1/1999 | Morser et al. | |

FOREIGN PATENT DOCUMENTS

| WO | WO 9726913 | 7/1997 |
| WO | WO 9739121 | 10/1997 |
| WO | WO 9739125 | 10/1997 |
| WO | WO 9907402 | 2/1999 |

OTHER PUBLICATIONS

Schmidt et al., "Regulation of Human Mononuclear Phagocyte Migration by Cell Surface–Binding Proteins for Advanced Glycosylation End Products," Journal of Clinical Investigation, 91(5):2155–2168, 1993.*
Brownlee, M. Diab. Care 15(12): 1835–1842, (Exhibit 2); Dec. 1992.
Neeper, M. Et al., J. Biol. Chem. 267: 14998–15004, (Exhibit 3); Jul. 1992.
Schmidt AM et al., J. Biol. Chem. 267: 14987–14997, (Exhibit 4); Jul. 1992.
Schmidt AM et al., Arterioscl. And Thromb. 14: 1521–1528 (Exhibit 5); Oct. 1994.
Schmidt, AM et al., Nat. Med. 1: 1002–1004 (Exhibit 6); Oct. 1995.
Schmidt, AM et al., PNAS (US) 91:8807–8811 (Exhibit 7); Sep. 1994.
Wautier, JL et al., J. Clin. Invest. 97: 238–243 (Exhibit 8), Jan. 1996.
Gibbons, G. H. and V. J. Dzau. (1996) . Molecular therapies for vascular diseases. *Science* 272: 689–693.
Nakamura, Y. et al. (1993) Immunohistochemical localization of advanced glycosylation endproducts in coronary atheroma and cardiac tissue in diabetes mellitus. Am. J. Pathol. 143(6):1649–1656.
Palinski, W. et al. (1995) Immunological evidence for the presence of advanced glycation end products in atherosclerotic lesions of euglycemic rabbits. *Arterioscl. Thromb. And Vasc. Biol.* 15(5):571–582.
Park, L., et al. (1998) "Suppression of accelerated diabetic atherosclerosis by soluble Receptor for AGE (sRAGE)" *Nature Medicine*, 4:1025–1031.
Renard, C., et al. (1997) . Recombinant advanced glycation end product receptor pharmacokinetics in normal and diabetic rats. Mol. Pharm. 52: 54–62.
Ritthaler, et al. (1995) Expression of receptors for advanced glycation end products in peripheral occulsive vascular disease. Am. J. Path. 146:688–694.
Schmidt, A. M. et al. (1993) Regulation of human mononuclear phagocyte migration by cell surface–binding proteins for advanced glycation end products. *J. Clin. Invest.* 92:2155–2168.
Schmidt, A. M., et al. (1994) "The endothelial cell binding site for advanced glycation endproducts consists of a complex: an integral membrane protein and a lactoferrin–like polypeptide" *J. Biol. Chem.*, 269:9882–9888.
Schmidt, A–M, et al. (1992) "Isolation and characterization of binding proteins for advanced glycation endproducts from lung tissue which are present on the endothelial cell surface" *J. Biol. Chem.*, 267:14987–14997.
Schmidt, A–M, et al. (1994) "Cellular receptors for advanced glycation end products" *Arterioscler. Thromb.*, 14:1521–1528.
Schmidt, A. M., et al (1995) "The Dark Side of Glucose (News and Views)" *Nature Medicine*, 1:1002–1004.

(List continued on next page.)

Primary Examiner—Mark Navarro
Assistant Examiner—Jana Hines
(74) Attorney, Agent, or Firm—John P. White; Cooper & Dunham LLP

(57) ABSTRACT

The present invention provides a method for treating symptoms of diabetes in a diabetic subject which comprises administering to the subject a therapeutically effective amount of an agent which inhibits binding of advanced glycation endproducts to any receptor for advanced glycation endproducts so as to treat chronic symptoms of diabetes in the subject.

11 Claims, 3 Drawing Sheets

OTHER PUBLICATIONS

Schmidt, A–M, et al. (1994) "Receptor for advanced glycation endproducts (AGEs) has a central role in vessel wall interactions and gene activation in response to circulating AGE proteins" *Proc. Natl. Acad. Sci. (USA)*, 91:8807–8811.

Schmidt, A. M., et al. (1995) "AGE interaction with their endothelial receptor induce expression of VCAM–1: a potential mechanism for the accelerated vasculopathy of diabetes" *J. Clin. Invest.*, 96:1395–1403.

Vlassara, H., et al. (1994). Pathogenic effects of advanced glycosylation: biochemical, biologic, and clinical implications for diabetes and aging. *Lab. Invest.* 70: 138–151.

Yang, Z., et al (1991) "Two novel rat liver membrane proteins that bind AGEs: relation to macrophage receptor for glucose–modified proteins" *J. Exp. Med.*, 174:515–524.

* cited by examiner ical analyses are shown comparing wound healing in the pres-
METHOD FOR TREATING SYMPTOMS OF DIABETES This application claims priority under 35 U.S.C §120 of CPA of U.S. Ser. No. 08/592,070, filed Jan. 26, 1996.

The invention disclosed herein was made with Government support under Grant Nos. HL21006 and AG00603 from the National Institutes of Health, U.S. Department of Health and Human Services. Accordingly, the U.S. Government has certain rights in this invention.

BACKGROUND OF THE INVENTION

Throughout this application, various publications are referenced by author and date. Full citations for these publications may be found listed alphabetically at the end of the specification immediately the claims. The disclosures of these publications in their entireties are hereby incorporated by reference into this application in order to more fully describe the state of the art as known to those skilled therein.

Ineffective healing of wounds is a serious problem in diabetes, contributing to increased morbidity (Reynolds, 1985; Galloway and Shuman, 1963; and Pearl and Kanat, 1988). The reparative response in wound healing is orchestrated by multiple cellular elements which work together in many ways, including infiltration of the lesion by inflammatory effector cells. Subsequent to this, fibroblastic elements together with inflammatory effector cells provide antibacterial mechanisms and promote removal of necrotic tissue, as well as laying down of new connective tissue. A fundamental disorder of glucose metabolism might perturb these complex and interactive protective processes. Previous work has suggested that cellular dysfunction in diabetic wound healing involves defective neutrophil function (Bagdade et al., 1978; Nolan et al., 1978; and Mowat and Baum, 1971), delayed infiltration of the wound with inflammatory cells (Greenhalgh et al., 1990 and Fahey et al., 1991), decreased production of collagen (Goodson and Hunt, 1977 and Goodson and Hunt, 1986), and diminished activity of endogenous growth factors, such as basic fibroblast growth factor (Giardino et al., 1994), which could provide a basis for the slower formation of granulation tissue and wound closure.

SUMMARY OF THE INVENTION

The present invention provides a method for treating symptoms of diabetes in a diabetic subject which comprises administering to the subject a therapeutic amount of an agent which inhibits binding of advanced glycation endproducts to any receptor for advanced glycation endproducts so as to treat symptoms of diabetes in the subject.

BRIEF DESCRIPTION OF THE FIGURES

FIG. 3A) and non-diabetic mice (db+/m+; FIG. 3B) were excised, fixed and sections stained with affinity-purified anti-AGE IgG. Magnification: 200×.

DETAILED DESCRIPTION OF THE INVENTION

Figure 1:
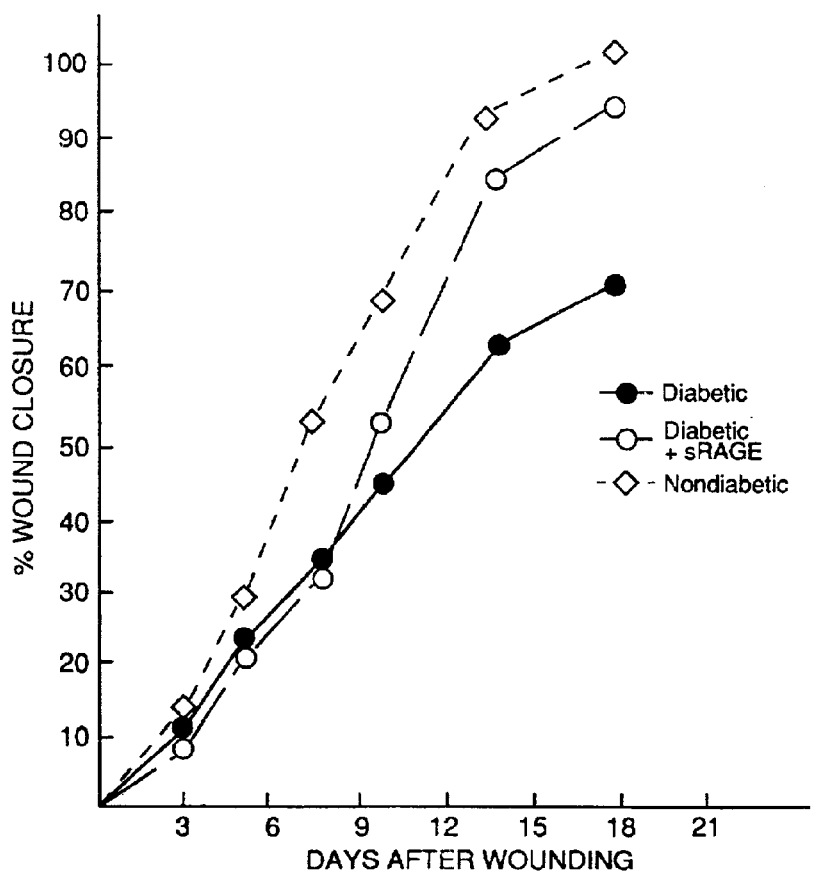
FIG. 1. Effect of sRAGE on wound healing in the genetically-diabetic db+/db+ mouse. A full-thickness 1.5× 1.5 cm wound was created on the backs of db+/db+ mice or control, heterozygote db+/m+mice and covered with TEGADERM®. Diabetic wounds were treated with either phosphate-buffered saline (PBS) directly under the TEGADERM® daily for 7 days commencing on day 3 following surgery or with sRAGE (200 ng). Wound area was measured at baseline through day 21 by placing a glass slide over the wound area, tracing the wound area, and placing this information into a computer in order to calculate the percentage of wound closure as a function of time. Left axis represents percent wound closure.

The present invention provides a method for treating symptoms of diabetes in a diabetic subject which comprises administering to the subject a therapeutically effective amount of sRAGE so as to treat symptoms of diabetes in the subject. The symptoms may comprise abnormal wound healing, symptoms of a heart attack, symptoms of a stroke, symptoms of peripheral vascular disease, amputation, symptoms of kidney disease, kidney failure, blindness, neuropathy, inflammation or impotence.

The present invention also provides a method for treating symptoms of diabetes in a diabetic subject which comprises administering to the subject a therapeutically effective amount of an agent which inhibits binding of advanced glycation endproducts to any receptor for advanced glycation endproducts so as to treat symptoms of diabetes in the subject. In accordance with the method of this invention, the agent may comprise a polypeptide, a peptidomimetic, an organic molecule, a carbohydrate, a lipid, an antibody or a nucleic acid. In accordance with the method of this invention, the polypeptide may comprise an advanced glycation endproduct polypeptide or a portion thereof, a receptor for an advanced glycation endproduct polypeptide or a portion thereof, a soluble receptor for advanced glycation endproduct polypeptide or a portion thereof. In accordance with the method of this invention, the antibody may comprise an anti-RAGE antibody or an anti-RAGE F(ab')$_2$ fragment. In accordance with the method of this invention, the therapeutically effective amount may comprise a dose of from about 200 ng/day/kg body weight to about 200,000 ng/day/kg body weight or from about 50 ng/day/kg to about 500,000 ng/day/kg body weight.

The present invention provides a method for improving wound healing in a diabetic subject which comprises administering to the subject a therapeutically effective amount of an agent which inhibits binding of advanced glycation endproducts to a receptor for advanced glycation endproducts, over a sufficient period of time in a sufficient amount so as to improve wound healing in the subject.

In accordance with the method of this invention, the agent may comprise a polypeptide, a peptidomimetic, an organic molecule, a carbohydrate, a lipid, an antibody or a nucleic acid. The polypeptide of this invention may comprise an advanced glycation endproduct polypeptide or a portion thereof, a receptor for advanced glycation endproduct polypeptide or a portion thereof, a soluble receptor for advanced glycation endproduct polypeptide or a portion thereof.

In one embodiment of this invention, the administration may comprise daily administration from about the day of wounding to about ten days after wounding. The present invention provides that the sufficient amount comprises a dose of from about 10 ng/day/kg body weight to about 500,000 ng/day/kg body weight or a dose of from about 150 ng/day/kg body weight to about 200,000 ng/day/kg body weight.

The present invention provides a method for treating symptoms of diabetes in a diabetic subject which comprises administering to the subject a therapeutically effective amount of an agent which agent inhibits binding of advanced glycation endproducts to any receptor for advanced glycation endproducts so as to treat symptoms of diabetes in the subject.

In accordance with the method of this invention, the agent may be a polypeptide, a peptidomimetic, an organic molecule, a carbohydrate, a lipid, an antibody or a nucleic acid. In the case of polypeptides, the polypeptide may be an advanced glycation endproduct (AGE) polypeptide or a portion thereof, a receptor for advanced glycation endproduct polypeptide or a portion thereof, a soluble receptor for advanced glycation endproduct polypeptide or a portion thereof, e.g., soluble RAGE, or a recombinant polypeptide. The polypeptide may be synthesized chemically or produced by standard recombinant DNA methods. In the case of antibodies, the antibody may be an anti-RAGE antibody or an anti-RAGE F(ab')$_2$ fragment.

In accordance with the method of the present invention, the symptoms which may be treated include abnormal wound healing, symptoms related to having a heart attack, such as chest pain, symptoms related to having a stroke, peripheral vascular disease, amputation, kidney disease, kidney failure, blindness, neuropathy, inflammation and impotence.

The subject on which the method is employed may be any mammal, e.g. a human, mouse, cow, pig, dog, cat, or monkey.

The administration of the agent may be effected by intralesional, intraperitoneal, intramuscular or intravenous injection; by infusion; or may involve liposome-mediated delivery; or topical, nasal, oral, anal, ocular or otic delivery.

In the practice of the method administration may comprise daily, weekly, monthly or hourly administration, the precise frequency being subject to various variables such as age and condition of the subject, amount to be administered, half-life of the agent in the subject, area of the subject to which administration is desired and the like.

In connection with the method of this invention, a therapeutically effective amount of may include dosages which take into account the size and weight of the subject, the age of the subject, the severity of the symptom, the surface area of the wound, the efficacy of the agent, the method of delivery of the agent and the history of the symptoms in the subject. One of ordinary skill in the art would be readily able to determine the exact dosages and exact times of administration based upon such factors. For example, a therapeutically effective amount may a dose of from about 200 ng/day/kg body weight to about 200,000 ng/day/kg body weight. In this regard, it has been shown that 24 micrograms administered intraperitoneally daily (on days 3–9) to wounded diabetic mice resulted in greatly improved wound healing. In this regard, the dose may also be administered as a single dose or as a series of doses over a period of time.

The present invention also provides a method for improving wound healing in a diabetic subject which comprises administering to the subject a therapeutically effective amount of an agent which inhibits binding of advanced glycation endproducts so as to improve wound healing in the subject.

The present invention provides a method for alleviating inflammation in a subject which comprises administering a therapeutically effective amount of an agent which inhibits binding of advanced glycation endproducts to any receptor for advanced glycation endproducts so as to treat symptoms of inflammation in the subject.

In accordance with the method of the invention, the agent may be a polypeptide, a peptidomimetic, an organic molecule, a carbohydrate, a lipid, an antibody or a nucleic acid. In the case of polypeptides, the polypeptide may be an advanced glycation endproduct polypeptide or a portion thereof, a receptor for advanced glycation endproduct polypeptide or a portion thereof, a soluble receptor for advanced glycation endproduct polypeptide or a portion thereof, or a recombinant polypeptide. The polypeptide may be synthesized chemically or produced by standard recombinant DNA methods. In the case of antibodies, the antibody may be an anti-RAGE antibody or an anti-RAGE F(ab')$_2$ fragment.

There may be other mechanisms by which soluble RAGE may improve diabetic wound healing. Soluble RAGE may have other effects, such as anti-inflammatory effects that are at least in part, independent of binding up AGE's and interfering with their ability to activate cellular RAGE.

The administration of the agent may be effected by intralesional, intraperitoneal, intramuscular or intravenous injection; by infusion; by liposome-mediated delivery or by topical, nasal, oral, anal, ocular or otic delivery.

In one embodiment of the claimed invention, the administration may include daily administration from about the day of wounding to about ten days after wounding.

In another embodiment of the invention, the sufficient amount may include a dose of from about 200 ng/day/mouse body weight to about 200,000 ng/day/mouse body weight.

The present invention also provides a method for improving wound healing in a diabetic subject which comprises administering to the subject a therapeutic amount of an agent so as to improve wound healing in the subject. The mechanism of improving wound healing may be biochemical in nature or competitive in nature.

As used herein "AGE" means an advanced glycation endproduct; "RAGE" means a receptor for an advanced glycation endproduct; "sRAGE" means a soluble form of a receptor for an advanced glycation endproducts, such as the extracellular two-thirds of the RAGE polypeptide.

Bovine nucleotide sequence of RAGE (SEQ ID NO:1):

```
CGGAGAAGGA TGGCAGCAGG GGCAGTGGTC GGAGCCTGGA TGCTAGTCCT CAGTCTGGGG    60
GGGACAGTCA CGGGGGACCA AAACATCACA GCCCGGATCG GGAAGCCACT GGTGCTGAAC   120
TGCAAGGGAG CCCCCAAGAA ACCACCCCAG CAGCTGGAAT GGAAACTGAA CACAGGCCGG   180
ACAGAAGCTT GGAAAGTCCT GTCTCCCCAG GGAGACCCCT GGGATAGCGT GGCTCGGGTC   240
CTCCCCAACG GCTCCCTCCT CCTGCCGGCT GTTGGGATCC AGGATGAGGG GACTTTCCGG   300
TGCCGGGCAA CGAGCCGGAG CGGAAAGGAG ACCAAGTCTA ACTACCGAGT CCGAGTCTAT   360
CAGATTCCTG GGAAGCCACA AATTGTTGAT CCTGCCTCTG AACTCATGGC TGGTGTCCCC   420
AATAAGGTGG GGACATGTGT GTCCGAGGGG GGCTACCCTG CAGGGACTCT TAACTGGCTC   480
TTGGATGGGA AACTCTGATT CCTGATGCCA AGGAGTGTC AGTGAAGGAA GAGACCAAGA   540
GACACCCAAA GACAGGGCTT TTCACTCTCC ATTCGGAGCT GATGGTGACC CCAGCTCGGG   600
GAGGAGCTCT CCACCCCACC TTCTCCTGTA GCTTCACCCC TGGCCTTCCC CGGCGCCGAG   660
CCCTGCACAC GGCCCCCATC CAGCTCAGGG TCTGGAGTGA GCACCGAGGT GGGGAGGGCC   720
CCAACGTGGA CGCTGTGCCA CTGAAGGAAG TCCAGTTGTG GTAGAGCCAG AAGGGGGAGC   780
AGTAGCTCCT GGTGGTACTG TGACCTTGAC CTGTGAAGCC CCCGCCCAGC CCCCACCTCA   840
AATCCACTGG ATCAAGGATG GCAGGCCCCT GCCCCTTCCC CCTGGCCCCA TGCTGCTCCT   900
CCCAGAGGTA GGGCCTGAGG ACCAGGGAAC CTACAGTTGT GTGGCCACCC ATCCCAGCCA   960
TGGGGGGGGA GAGAGCCGTG CTGTCAGCGT CACGATCATC GAAACAGGCG AGGAGGGGAC  1020
GACTGCAGGC TCTGTGGAAG GGCCGGGGCT GGAAACCTAG CCCTGACCCT GGGGATCCTG  1080
GGAGGCCTGG GGACAGTCGC CCTGCTCATT GGGGTCATCG TGTGGCATCG AAGGCCGGCA  1140
ACGCAAAGGA CAGGAGAGGA AGGTCCCGGA AAACCAGGAG GAGGAAGAGG AGGAGAGAGC  1200
GGAACTGAAC CAGCCAGAGG AGCCCGAGGC GGCAGAGAGC AGCACAGGAG GGCCTTGAGG  1260
AGCCCACGGC CAGACCCGAT CCATCAGCCC CTTTTCTTTT CCCACACTCT GTTCTGGCCC  1320
CAGACCAGTT CTCCTCTGTA TAATCTCCAG CCCACATCTC CCAAACTTTC TTCCACAACC  1380
AGAGCCTCCC ACAAAAAGTG ATGAGTAAAC ACCTGCCACA TTTAAAAAAA AAAAAAAA    1438
```

Bovine amino acid sequence of RAGE (SEQ ID NO:2):

```
Met Ala Ala Gly Ala Val Val Gly Ala Trp Met Leu Val Leu Ser Leu
1               5                   10                  15

Gly Gly Thr Val Thr Gly Asp Gln Asn Ile Thr Ala Arg Ile Gly Lys
            20                  25                  30

Pro Leu Val Leu Asn Cys Lys Gly Ala Pro Lys Lys Pro Pro Gln Gln
        35                  40                  45

Leu Glu Trp Lys Leu Asn Thr Gly Arg Thr Glu Ala Trp Lys Val Leu
10  50                  55                  60

Ser Pro Gln Gly Asp Pro Trp Asp Ser Val Ala Arg Val Leu Pro Asn
65                  70                  75                  80

Gly Ser Leu Leu Leu Pro Ala Val Gly Ile Gln Asp Glu Gly Thr Phe
                85                  90                  95

Arg Cys Arg Ala Thr Ser Arg Ser Gly Lys Glu Thr Lys Ser Asn Tyr
            100                 105                 110

Arg Val Arg Val Tyr Gln Ile Pro Gly Lys Pro Glu Ile Val Asp Pro
        115                 120                 125

Ala Ser Glu Leu Met Ala Gly Val Pro Asn Lys Val Gly Thr Cys Val
    130                 135                 140
```

-continued

```
Ser Glu Gly Gly Tyr Pro Ala Gly Thr Leu Asn Trp Leu Leu Asp Gly
145                 150                 155                 160

Lys Thr Leu Ile Pro Asp Gly Lys Gly Val Ser Val Lys Glu Glu Thr
            165                 170                 175

Lys Arg His Pro Lys Thr Gly Leu Phe Thr Leu His Ser Glu Leu Met
        180                 185                 190

Val Thr Pro Ala Arg Gly Gly Ala Leu His Pro Thr Phe Ser Cys Ser
    195                 200                 205

Phe Thr Pro Gly Leu Pro Arg Arg Arg Ala Leu His Thr Ala Pro Ile
    210                 215                 220

Gln Leu Arg Val Trp Ser Glu His Arg Gly Gly Glu Gly Pro Asn Val
225                 230                 235                 240

Asp Ala Val Pro Leu Lys Glu Val Gln Leu Val Val Glu Pro Glu Gly
            245                 250                 255

Gly Ala Val Ala Pro Gly Gly Thr Val Thr Leu Thr Cys Glu Ala Pro
            260                 265                 270

Ala Gln Pro Pro Pro Gln Ile His Trp Ile Lys Asp Gly Arg Pro Leu
        275                 280                 285

Pro Leu Pro Pro Gly Pro Met Leu Leu Leu Pro Glu Val Gly Pro Glu
    290                 295                 300

Asp Gln Gly Thr Tyr Ser Cys Val Ala Thr His Pro Ser His Gly Pro
305                 310                 315                 320

Gln Glu Ser Arg Ala Val Ser Val Thr Ile Ile Glu Thr Gly Glu Glu
            325                 330                 335

Gly Thr Thr Ala Gly Ser Val Glu Gly Pro Gly Leu Glu Thr Leu Ala
            340                 345                 350

Leu Thr Leu Gly Ile Leu Gly Gly Leu Gly Thr Val Ala Leu Leu Ile
        355                 360                 365

Gly Val Ile Val Trp His Arg Arg Gln Arg Lys Gly Gln Glu Arg
370                 375                 380

Lys Val Pro Glu Asn Gln Glu Glu Glu Glu Glu Arg Ala Glu Leu
385                 390                 395                 400

Asn Gln Pro Glu Glu Pro Glu Ala Ala Glu Ser Ser Thr Gly Gly Pro
            405                 410                 415
```

Human nucleotide sequence of RAGE (SEQ ID NO: 3)

```
GGGGCAGCCG GAACAGCAGT TGGAGCCTGG GTGCTGGTCC TCAGTCTGTG GGGGGCAGTA   60

GTAGGTGCTC AAAACATCAC AGCCCGGATT GGCGAGCCAC TGGTGCTGAA GTGTAAGGGG  120

GCCCCCAAGA AACCACCCCA GCGGCTGGAA TGGAAACTGA ACACAGGCCG ACAGAAGCT  180

TGGAAGGTCC TGTCTCCCCA GGGAGGAGGC CCCTGGGACA GTGTGGCTCG TGTCCTTCCC  240

AACGGCTCCC TCTTCCTTCC GGCTGTCGGG ATCCAGGATG AGGGGATTTT CCGGTGCAGG  300

GCAATGAACA GGAATGGAAA GGAGACCAAG TCCAACTACC GAGTCCGTGT CTACCAGATT  360

CCTGGGAAGC CAGAAATTGT AGATTCTGCC TCTGAACTCA CGGCTGGTGT TCCCAATAAG  420

GTGGGGACAT GTGTGTCAGA GGGAAGCTAC CCTGCAGGGA CTCTTAGCTG GCACTTGGAT  480

GGGAAGCCCC TGGTGCCTAA TGAGAAGGGA GTATCTGTGA AGGAACAGAC CAGGAGACAC  540

CCTGAGACAG GGCTCTTCAC ACTGCAGTCG GAGCTAATGG TGACCCCAGC CCGGGGAGGA  600

GATCCCCGTC CCACCTTCTC CTGTAGCTTC AGCCCAGGCC TTCCCCGACA CCGGGCCTTG  660

CGCACAGCCC CCATCCAGCC CCGTGTCTGG GAGCCTGTGC CTCTGGAGGA GGTCCAATTG  720

GGTGGTGGAG CCAGAAGGTG GAGCAGTAGC TCCTGGTGGA ACCGTAACCC TGACCTGTGA  780
```

-continued

```
AGTCCCTGCC CAGCCCTCTC CTCAAATCCA CTGGATGAAG GATGGTGTGC CCTGCCCCTT    840

CCCCCCAGCC CTGTGCTGAT CCTCCCTGAG ATAGGGCCTC AGGACCAGGG AACCTACAGC    900

TGTGTGGCCA CCCATTCCAG CCACGGGCCC CAGGAAAGCC GTGCTGTCAG CATCAGCATC    960

ATCGAACCAG GCGAGGAGGG GCCAACTGCA GGCTCTGTGG GAGGATCAGG GCTGGGAACT   1020

CTAGCCCTGG CCCTGGGGAT CCTGGGAGGC CTGGGGACAG CCGCCCTGCT CATTGGGGTC   1080

ATCTTGTGGC AAAGGCGGCA ACGCCGAGGA GAGGAGAGGA GGCCCCAGAA AACCAGGAGG   1140

AAGAGGAGGA GCGTGCAGAA CTGAATCAGT CGGAGGAACC TGAGGCAGGC GAGAGTACTA   1200

CTGGAGGGCC TTGAGGGGCC CACAGACAGA TCCCATCCAT CAGCTCCCTT TTCTTTTTCC   1260

CTTGAACTGT TCTGGCCTCA GACCAACTCT CTCCTGTATA ATCTCTCTCC TGTATAACCC   1320

CACCTTGCCA AGCTTTCTTC TACAACCAGA GCCCCCACA ATGATGATTA AACACCTGAC   1380

ACATCTTTGC AAAAAAAAAA AAAAA                                         1405
```

Human amino acid sequence of RAGE (SEQ ID NO:4):

```
Gly Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Gly Pro Trp Asp Ser Val Ala Arg Val Leu Pro
65              70                  75                  80

Asn Gly Ser Leu Phe Leu Pro Ala Val Gly Ile Gln Asp Glu Gly Ile
                85                  90                  95

Phe Arg Cys Arg Ala Met Asn Arg Asn Gly Lys Glu Thr Lys Ser Asn
                100                 105                 110

Tyr Arg Val Arg Val Tyr Gln Ile Pro Gly Lys Pro Glu Ile Val Asp
            115                 120                 125

Ser Ala Ser Glu Leu Thr Ala Gly Val Pro Asn Lys Val Gly Thr Cys
130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
        195                 200                 205

Ser Phe Ser Pro Gly Leu Pro Arg His Arg Ala Leu Arg Thr Ala Pro
    210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
                245                 250                 255

Leu Thr Cys Glu Val Pro Ala Gln Pro Ser Pro Gln Ile His Trp Met
            260                 265                 270

Lys Asp Gly Val Pro Leu Pro Leu Pro Pro Ser Pro Val Leu Ile Leu
        275                 280                 285
```

```
                           -continued
Pro Glu Ile Gly Pro Gln Asp Gln Gly Thr Tyr Ser Cys Val Ala Thr
    290             295                 300

His Ser Ser His Gly Pro Gln Glu Ser Arg Ala Val Val Ser Ile Ser
305             310                 315                 320

Ile Ile Glu Pro Gly Glu Glu Gly Pro Thr Ala Gly Ser Val Gly Gly
                325                 330                 335

Ser Gly Leu Gly Thr Leu Ala Leu Ala Leu Gly Ile Leu Gly Gly Leu
                340                 345                 350

Gly Thr Ala Ala Leu Leu Ile Gly Val Ile Leu Trp Gln Arg Arg Gln
            355                 360                 365

Arg Arg Gly Glu Glu Arg Lys Ala Pro Glu Asn Gln Glu Glu Glu Glu
        370                 375                 380

Glu Arg Ala Glu Leu Asn Gln Ser Glu Glu Pro Glu Ala Gly Glu Ser
385                 390                 395                 400

Ser Thr Gly Gly Pro
                405
```

In the practice of the methods of the invention a "therapeutically effective amount" is an amount which is capable of inhibiting the binding of AGE to any receptor for advanced glycation endproduct. Accordingly, the effective amount will vary with the subject being treated, as well as the condition to be treated. For the purposes of this invention, the methods of administration are to include, but are not limited to, administration cutaneously, subcutaneously, intravenously, parenterally, orally, topically, or by aerosol.

Portions of the agent of the invention may be "labeled" by association with a detectable marker substance (e.g., radiolabeled with $^{125}$I or biotinylated) to provide reagents useful in detection and quantification of such agent or its receptor bearing cells or its derivatives in solid tissue and fluid samples such as blood, cerebral spinal fluid or urine.

The administration of compounds and pharmaceuticals to subjects to improve wound healing is known in the art because the need for improving the symptoms associated with diabetes has been a long-felt need. The following publications are hereby incorporated by reference: U.S. Pat. No. 5,561,116, Solid product containing propolis components, and preparation and uses thereof; U.S. Pat. No. 4,971,954, Collagen-based matrices ribose cross-linked; U.S. Pat. No. 5,567,417, Method for inhibiting angiogenesis using heparinase; U.S. Pat. No. 5,565,428, Method of administration of IGF-1. Administering insulin-like growth factor-I to a mammal so as to sustain its biological activity in the mammal comprising administering a therapeutically effective amount of IGF-I to the mammal for a period of time that stimulates the maximum biological response in the mammal is disclosed. The '428 patent also discloses administration over a period of time and repeated administration and discontinuance of administration for a period as long as necessary to achieve or maintain the desired biological response in the mammal. Thus, methods of administration of therapeutic amounts of a peptide or protein are known to one of skill in the art. U.S. Pat. No. 5,561,137, Thio-heterocyclic macrolactam immunomodulators; U.S. Pat. No. 5,561,110, Method for the treatment of the complications and pathology of diabetes; U.S. Pat. No. 5,547,672, Accelerated wound healing; U.S. Pat. No. 5,532,227, Tetracyclines including non-antimicrobial chemically-modified tetracyclines inhibit excessive glycosylation of different types of collagen and other proteins during diabetes; U.S. Pat. No. 5,527,772 Regulation of cell proliferation and differentiation using peptides; U.S. Pat. No. 5,468,737, Wound healing accelerated by systemic administration of polysaccharide from aloe; U.S. Pat. No. 5,395,398, Microelectric apparatus for the antisepsis, promulgation of healing and analgesia of wound and chronic skin ulcers; U.S. Pat. No. 5,378,475, Sustained release drug delivery devices; U.S. Pat. No. 5,246,708, Methods for promoting wound healing with deoxyribonucleosides; U.S. Pat. No. 5,532,227, Tetracycline, including non-antimicrobial chemically-modified tetracycline inhibit excessive glycosylation of different types of collagen and other proteins during diabetes. The disclosures of the publications referred to herein, in their entireties, are hereby incorporated by reference into this application in order to more fully describe the state of the art as known to those skilled therein.

When administered, compounds are often cleared rapidly from the circulation and may therefore elicit relatively short-lived pharmacological activity. Consequently, frequent injections of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently or in lower doses than with the unmodified compound.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The compound of the present invention capable of improving wound healing in a subject may be delivered in a microencapsulation device so as to reduce or prevent a host immune response against the compound or against cells which may produce the compound. The compound of the present invention may also be delivered microencapsulated in a membrane, such as a liposome.

Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

The invention also provides a kit which comprises a therapeutic amount of an agent, which agent is capable of inhibiting binding of advanced glycation endproducts to a receptor for advanced glycation endproducts, over a sufficient period of time in a sufficient amount so as to treat chronic symptoms of diabetes in the subject. A kit may include a composition which includes sRAGE or a portion thereof in a form which is previously dose regulated and time regulated so that a subject may easily take such therapeutic at home or away from a clinical setting.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

EXAMPLE 1

Improved Wound Healing in Diabetic Mice by Treatment with the Soluble Receptor for Advanced Glycation Endproducts (sRAGE)

Defective wound healing in diabetes continues to be an important cause of morbidity in the postoperative period, following trauma, and in the repair of cutaneous lesions. Advanced Glycation Endproducts (AGEs) are the result of nonenzymatic glycation/oxidation of proteins/lipids. Accelerated formation and accumulation of AGEs in tissues of patients with diabetes has been linked, in certain situations, to the development of secondary complications. An important means by which AGEs perturb homeostatic processes is through their interaction with cellular binding sites; the best characterized of these is Receptor for AGE or RAGE, an immunoglobulin superfamily molecule expressed by endothelium, monocytes, and smooth muscle cells, as well as mesangial cells and neurons. AGE engagement of RAGE leads to endothelial activation, with expression of adhesion molecules, enhanced procoagulant properties, and diminished barrier function; and perturbation of monocytes, with changes in cell motility and activation, resulting in expression of proinflammatory cytokines. The interaction of AGEs with RAGE-bearing cells, especially endothelium and mononuclear phagocytes, may promote chronic cellular activation thereby preventing optimal wound healing as reflected by formation of granulation tissue and new connective tissue. The data herein are consistent with this concept: using a secondary intention wound model in diabetic mice, wound closure is enhanced following administration of soluble(s) RAGE, the extracellular domain of the receptor. These experiments contribute to a long-term goal and long-felt need, understanding the contribution of cellular interactions of AGEs in the pathogenesis of diabetic complications.

Poor wound healing in diabetes is likely to be a manifestation of a basic defect in the host inflammatory-reparative response, in addition to possible underlying vascular insufficiency. Exposure of macromolecules to aldose sugars results in nonenzymatic glycation and oxidation (Baynes, 1991; Sell and Monnier, 1989; Ruderman et al., 1992; and Vlassara et al., 1994), initially the reversible early glycation adducts, Schiff bases and Amadori products, form. Following further complex molecular rearrangements, the irreversible AGEs come about. The latter comprise a heterogenous group of structures characterized by fluorescence, propensity to form cross-links, generation of reactive oxygen intermediates (ROIs) and interaction with cellular receptors, the best characterized of which is Receptor for AGE, or RAGE (Schmidt et al., 1992; Neeper et al., 1992; and Schmidt et al., 1994a). AGEs accumulated in the tissues in diabetes influence end-organ function by two general mechanisms: directly, via effects on tissue architecture, consequent to the formation of cross-links and trapping of plasma proteins, and indirectly, by interaction with cellular elements, such as endothelial cells (Ecs), mononuclear phagocytes (Mps), central to homeostasis as well as the host response to pathophysiologically relevant stimuli.

Studies have suggested that the extracellular two-thirds of the molecule, soluble or sRAGE, appeared to be able to inhibit the interaction of circulating AGEs with cellular surfaces (Schmidt et al., 1994b). For example, binding of radiolabelled AGE albumin, a prototypic ligand developed in the laboratory, to cultured endothelial cells or peripheral blood-derived mononuclear phagocytes, was inhibited in the presence of increasing doses of sRAGE. In vivo, clearance of radiolabelled AGE albumin from the circulation of a normal mouse after intravenous injection, was delayed upon treatment with sRAGE. Extrapolation of these findings was attempted to the setting of wound healing. The goal in these studies was to assess the role of AGE-RAGE interaction in the setting of the host response to wounding.

In order to assess the contribution of AGE-RAGE interaction to defective wound healing in diabetes, the wound healing response in diabetic was compared to normal animals, and to determine if blockade of RAGE would ameliorate wound closure in diabetes. In these studies, it was found that administration of soluble RAGE improved wound healing in genetically-diabetic mice. These data support the hypothesis that RAGE blockade may represent a feasible target for intervention in diabetic wound healing as well as other complications of diabetes, such as renal, retinal, neurological, cardiovascular, cerebrovascular and peripheral vascular diseases. Diabetic subjects experience increased restenosis and local problems after angioplasty which suggests that soluble RAGE may be beneficial in reducing restenosis after balloon/stent injury.

Materials and Methods

Murine Model of Diabetes

A genetic model of insulin-resistant/hyperglycemic diabetes (db+/db+mice) due to an autosomal recessive trait (chromosome 4) which results in abnormalities of glucose metabolism and obesity in homozygote mice was employed. Heterozygote mice (db+/+m) do not develop these abnormalities, and are employed as controls (Coleman, 1982 and Wyse and Dulin, 1970). Diabetic animals are hyperglycemic (glucose>400 mg/dl by age 3 months), and develop abnormalities similar to human complications, including a defective wound repair. Life expectancy of homozygote mice is 6–8 months. Wounding studies began when mice reached 8 weeks of age, as AGEs are present by that time.

Model of Wound Healing

For analysis of wound healing in diabetes, a secondary intention wound model was employed (Greenhalgh et al., 1990), as it stimulates, in part, the clinical situation following breakdown of skin in an ulcerated area. A full-thickness 1.5×1.5 cm wound was created on the back of the mouse which was subsequently covered by TEGADERM (clear, plastic closure). The initial area of the wound was measured by placing a sterile glass slide over the area, and tracing the edges of the wound. The area was then determined by using a computer program (NIH Image 157). Serial measurement of the wound dimensions were made on days 3,5,7,10,14, and 17. This data, consistent with those of previous studies (Greenhalgh et al., 1990), showed significant delay of wound repair in the diabetic mouse especially within the first 2–3 weeks after creation of the wound. Animals in each group were sacrificed at days 17 for analysis. Studies began when mice reached 8–10 weeks of age. In certain experiments, mice were treated with soluble RAGE (the extracellular two-thirds of the molecule) under the TEGADERM on days 3 through 9 after the initial wounding procedure.

Immunohistochemistry for Detection of Advanced Glycation Endproducts

At the time of the wounding procedure, 1.5×1.5 cm wounds were excised, fixed in formalin (10%) and then processed for immunohistochemistry using affinity-purified anti-AGE IgG (Miyata et al., 1996).

Results

In order to understand the role of RAGE in diabetic wound healing, 1.5×1.5 cm wounds were created on the backs of db+/db+ or db+/m+mice. It was first determined that there was no statistically-significant difference in original wound area among the groups of mice receiving the various treatment regimens. When sRAGE (200 ng/day) was administered under the TEGADERM daily from days 3 through 9, the wound healing observed in diabetic mice was significantly enhanced compared with diabetic mice treated with vehicle (phosphate buffered saline; $p<0.05$; FIG. 1). Furthermore, the healing observed in diabetic mice treated with sRAGE approximated that observed in control, db+/m+mice treated with vehicle (differences were not statistically significant). (FIG. 1).

Figure 2:
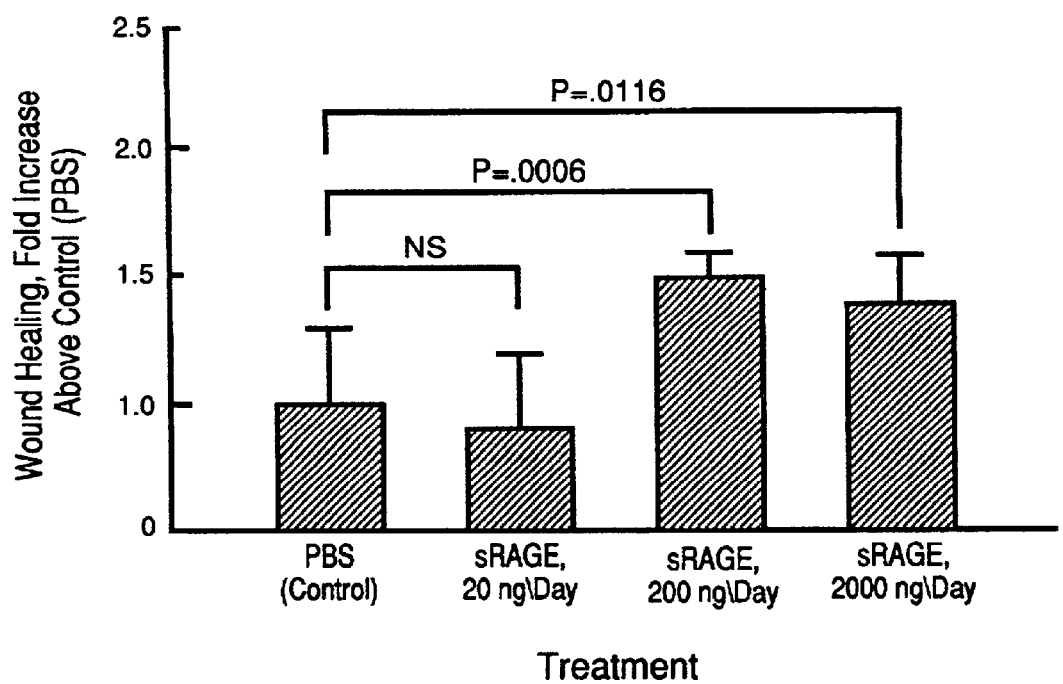
FIG. 2. Administration of sRAGE to the genetically-diabetic db+/db+mouse improves wound healing: dose-response studies. Wounds were created as above and treated from days 3 through 9 with sRAGE (either 2,000, 200, or 20 ng/day) or with phosphate-buffered saline. At day 10, wound area was measured and compared with initial wound area as above. Results are presented as fold increase in percent wound healing compared with mice treated with phosphate buffered saline (defined as one in figure). All statistical analyses are shown comparing wound healing in the presence of different doses of sRAGE vs. treatment of diabetic wounds with phosphate-buffered saline.

Consistent with the hypothesis that these findings were due to receptor-mediated mechanisms, dose-response studies revealed that there was no enhancement of diabetic wound healing upon administration of sRAGE, 2,000 ng/day, compared with a daily dose of 200 ng/day (differences were not significant; FIG. 2). However, consistent with the studies described herein in diabetic mice, treatment with either 200 or 2,000 ng/day sRAGE (administered on days 3 through 9) was significantly superior to treatment of these mice with phosphate buffered saline when the final wound area was measured on day ten after creation of the wound (FIG. 2). However, at a daily dose of sRAGE of 20 ng/day, there was no significant difference in wound healing in the diabetic mice receiving sRAGE versus those diabetic mice receiving vehicle. (FIG. 2).

Figures 3A, 3B:
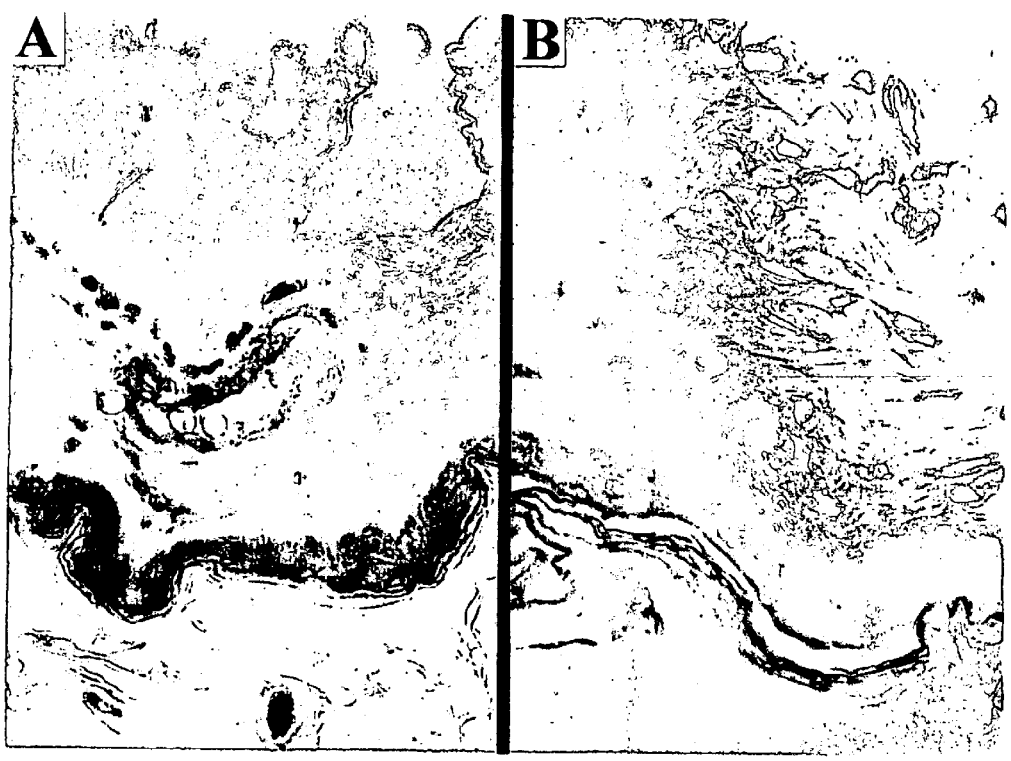
FIGS. 3A and 3B. AGE-immunoreactive epitopes in the wounds of diabetic (db+/db+) mice. 1.5×1.5 cm full-thickness wounds created in the backs of diabetic mice (db+/db+ mice.

In order to determine if diabetic wounds were enriched in AGE-immunoreactive material, immunohistochemistry was performed of diabetic versus control mice wounds using affinity-purified anti-AGE IgG. These studies demonstrated that there was a significant increase in AGE-reactive material in the wound tissue of the diabetic mice (FIG. 3A) compared with the nondiabetic control animals (FIG. 3B).

Discussion

The results of these studies indicate that in diabetic tissue such as wounds, there is increased deposition/formation of AGEs. Such AGEs, upon interaction with their cellular receptor RAGE, result in the generation of a sustained inflammatory environment in which healing and quiescence of the potent effector cells and mediators is markedly delayed. It was hypothesized that interference with AGE-RAGE interaction might result in accelerated healing. In these studies, it was demonstrated that local administration of soluble RAGE improved diabetic wound healing in a dose-dependent manner. The specific mechanisms which underlie the efficacy of administration of sRAGE is important. It is possible that administration of sRAGE improves any one of a number of important steps in physiologic wound healing such as inflammation, angiogenesis and/or formation and deposition of new granulation tissue, specifically collagen.

Taken together, these data suggest that in an AGE-enriched environment such as that observed in diabetes, interference with AGE-cellular RAGE interaction might result in amelioration of the chronic complications of diabetes. Given that RAGE is expressed in the endothelium and smooth muscle of the vasculature, in mesangial cells, in certain neural and vascular cells of the retina, and in certain neurons of both the central and peripheral nervous systems as well as other cells, it is likely that blockade of cellular RAGE might result in improved diabetic complications that might otherwise lead to heart attacks, stroke, peripheral vascular disease, amputation of the extremities, kidney disease/failure, blindness, impotence and neuropathy. RAGE is found in monocytes and macrophages and may be present in other cell types wherein therapeutic intervention may also be possible. The present studies support the concept that administration of sRAGE (or other forms of RAGE blockade; such as recombinant sRAGE, RAGE-based peptides, anti-RAGE IgG or anti-RAGE $F(ab')_2$) might present a novel form of therapeutic intervention in this chronic, debilitating disorder.

References

Bagdade, J. et al. (1978) Impaired granulocyte adherence. A reversible defect in host defense in patients with poorly controlled diabetes. Diabetes 27:677–681.

Baynes, J. (1991) Role of oxidative stress in development of complications in diabetes. Diabetes 40:405–412.

Coleman, D. (1982) Diabetes-obesity syndromes in mice. Diabetes 31 (Suppl.):1–6.

Fahey, T. et al. (1991) Diabetes impairs the late inflammatory response to wound healing. Surg. Res. 50:308–313.

Galloway, J. and Shuman, D. (1963) Diabetes and Surgery. Am. J. Med. 34:177–191.

Giardino, I. et al. (1994) Nonenzymatic glycosylation in vitro and in bovine endothelial cells after basic fibroblast growth factor activity. J. Clin. Invest. 94:110–117.

Goodson, W. and Hunt T. (1977) Studies of wound healing in experimental diabetes mellitus. J. Surg. Res. 22:221–227.

Goodson, W. and Hunt T. (1986) Wound collagen accumulation in obese hyperglycemic mice. Diabetes 35:491–495.

Greenhalgh, D. et al. (1990) PDGF and FGF stimulate wound healing in the genetically diabetic mouse. Am. J. Pathol. 136:1235–1246.

Mowat, A. and Baum, J. (1971) Chemotaxis of polymorphonuclear leukocytes from patients with diabetes mellitus. NEJM 284:621–627.

Neeper, M. et al. (1992) Cloning and expression of RAGE: a cell surface receptor for AGEs. J. Biol. Chem. 267:14998–15004.

Nolan, C. et al. (1978) Further characterization of the impaired bactericidal function of granulocytes in patients with poorly controlled diabetes. Diabetes 27:889–894.

Pearl, S. and Kanat, I. (1988) Diabetes and healing: a review of the literature. J. Foot Surg. 27:268–273.

Reynolds, C. (1985) Management of the diabetic surgical patient. A systematic but flexible plan is the key. Postgrad. Med. 77:265–279.

Ruderman, N. et al. (1992) Glucose and diabetic vascular disease. FASEB J. 6:2905–2914.

Schmidt, A-M et al. (1994a) Cellular receptors for AGEs. Arterioscler. Thromb. 14:1521–1528.

Schmidt, A-M. et al. (1994b) RAGE has a central role in vessel wall interactions and gene activation in response to AGESs. PNAS, USA 91:8807–8811.

Schmidt, A-M et al. (1992) Isolation and characterization of binding proteins for AGEs from lung tissue which are present on the endothelial surface. J. Biol. Chem. 267:14987–14997.

Sell, D. and Monnier, V. (1989) Structure elucidation of senescence cross-link from human extracellular matrix. J. Biol. Chem. 264:21597–21602.

Vlassara, H. et al. (1994) Pathogenic effects of AGEs:biochemical, biologic, and clinical implications for diabetes and aging. Lab. Invest. 70:138–151.

Wyse, B. and Dulin, W. (1970) The influence of age and dietary conditions on diabetes in the Db mouse. Diabetologia 6:268–273.

What is claimed is:

1. A method for enhancing wound closure in a diabetic subject which comprises administering to the subject a therapeutically effective amount of human soluble Receptor for Advanced Glycation Endproduct (sRAGE) which inhibits binding of advanced glycation endproducts to RAGE so as to enhance wound closure in a diabetic subject.

2. The method of claim 1, wherein the subject is a mammal.

3. The method of claim 2, wherein the mammal is a human.

4. The method of claim 1, wherein the administration is via intralesional, intraperitoneal, intramuscular or intravenous injection; infusion; liposome-mediated delivery; topical, nasal, oral, anal, ocular or otic delivery.

5. The method of claim 1, wherein the soluble form of RAGE is administered daily.

6. The method of claim 1, wherein the amount comprises a dose of from about 200 ng/day/kg body weight to about 200,000 ng/day/kg body weight.

7. The method of claim 1, wherein the administration comprises daily administration from about the day of wounding to about ten days after wounding.

8. The method of claim 1, wherein the amount comprises a dose of from about 10 ng/day/kg body weight to about 500,000 ng/day/kg body weight.

9. The method of claim 1, wherein the amount comprises a dose of from about 150 mg/day/kg body weight to about 200,000 ng/day/kg body weight.

10. The method of claim 1, wherein the soluble form of RAGE comprises a portion of soluble RAGE.

11. The method of claim 1, wherein the soluble form of RAGE comprises the extracellular two-thirds of the RAGE polypeptide.

* * * * *

SEQUENCE LISTING

```
<160> NUMBER OF SEQ ID NOS: 4

<210> SEQ ID NO 1
<211> LENGTH: 1438
<212> TYPE: DNA
<213> ORGANISM: Bovine

<400> SEQUENCE: 1
cggagaagga tggcagcagg ggcagtggtc ggagcctgga tgctagtcct cagtctgggg      60
gggacagtca cggggacca aaacatcaca gcccggatcg ggaagccact ggtgctgaac      120
tgcaagggag cccccaagaa accacccag cagctggaat ggaaactgaa cacaggccgg      180
acagaagctt ggaaagtcct gtctccccag ggagaccct gggatagcgt ggctcgggtc      240
ctccccaacg gctccctcct cctgccggct gttgggatcc aggatgaggg gactttccgg      300
tgccgggcaa cgagccggag cggaaaggag accaagtcta actaccgagt ccgagtctat     360
cagattcctg ggaagccaga aattgttgat cctgcctctg aactcatggc tggtgtcccc      420
aataaggtgg ggacatgtgt gtccgagggg ggctaccctg cagggactct taactggctc     480
ttggatggga aactctgatt cctgatggca aaggagtgtc agtgaaggaa gagaccaaga     540
gacacccaaa gacagggctt ttcactctcc attcggagct gatggtgacc ccagctcggg     600
gaggagctct ccaccccacc ttctcctgta gcttcacccc tggccttccc cggcgccgag     660
ccctgcacac ggccccccatc cagctcaggg tctggagtga gcaccgaggt ggggagggcc    720
ccaacgtgga cgctgtgcca ctgaaggaag tccagttgtg gtagagccag aaggggggagc   780 agtagctcct ggtggtactg tgaccttgac ctgtgaagcc cccgcccagc ccccacctca    840
aatccactgg atcaaggatg gcaggcccct gccccttccc cctggcccca tgctgctcct    900
cccagaggta gggcctgagg accagggaac ctacagttgt gtggccaccc atcccagcca    960 tggggggggag gagagccgtg ctgtcagcgt cacgatcatc gaaacaggcg aggaggggac    1020
gactgcaggc tctgtggaag ggccggggct ggaaacctag ccctgaccct gggatcctg    1080
```

-continued

```
ggaggcctgg ggacagtcgc cctgctcatt ggggtcatcg tgtggcatcg aaggccggca    1140
acgcaaagga caggagagga aggtcccgga aaaccaggag gaggaagagg aggagagagc    1200
ggaactgaac cagccagagg agcccgaggc ggcagagagc agcacaggag ggccttgagg    1260
agcccacggc cagacccgat ccatcagccc cttttctttt cccacactct gttctggccc    1320
cagaccagtt ctcctctgta taatctccag cccacatctc ccaaactttc ttccacaacc    1380
agagcctccc acaaaaagtg atgagtaaac acctgccaca tttaaaaaaa aaaaaaaa      1438
```

<210> SEQ ID NO 2
<211> LENGTH: 416
<212> TYPE: PRT
<213> ORGANISM: Bovine

<400> SEQUENCE: 2

```
Met Ala Ala Gly Ala Val Val Gly Ala Trp Met Leu Val Leu Ser Leu
1               5                   10                  15

Gly Gly Thr Val Thr Gly Asp Gln Asn Ile Thr Ala Arg Ile Gly Lys
            20                  25                  30

Pro Leu Val Leu Asn Cys Lys Gly Ala Pro Lys Lys Pro Pro Gln Gln
        35                  40                  45

Leu Glu Trp Lys Leu Asn Thr Gly Arg Thr Glu Ala Trp Lys Val Leu
    50                  55                  60

Ser Pro Gln Gly Asp Pro Trp Asp Ser Val Ala Arg Val Leu Pro Asn
65                  70                  75                  80

Gly Ser Leu Leu Leu Pro Ala Val Gly Ile Gln Asp Glu Gly Thr Phe
                85                  90                  95

Arg Cys Arg Ala Thr Ser Arg Ser Gly Lys Glu Thr Lys Ser Asn Tyr
            100                 105                 110

Arg Val Arg Val Tyr Gln Ile Pro Gly Lys Pro Glu Ile Val Asp Pro
        115                 120                 125

Ala Ser Glu Leu Met Ala Gly Val Pro Asn Lys Val Gly Thr Cys Val
    130                 135                 140

Ser Glu Gly Gly Tyr Pro Ala Gly Thr Leu Asn Trp Leu Leu Asp Gly
145                 150                 155                 160

Lys Thr Leu Ile Pro Asp Gly Lys Gly Val Ser Val Lys Glu Glu Thr
                165                 170                 175

Lys Arg His Pro Lys Thr Gly Leu Phe Thr Leu His Ser Glu Leu Met
            180                 185                 190

Val Thr Pro Ala Arg Gly Gly Ala Leu His Pro Thr Phe Ser Cys Ser
        195                 200                 205

Phe Thr Pro Gly Leu Pro Arg Arg Arg Ala Leu His Thr Ala Pro Ile
    210                 215                 220

Gln Leu Arg Val Trp Ser Glu His Arg Gly Glu Gly Pro Asn Val
225                 230                 235                 240

Asp Ala Val Pro Leu Lys Glu Val Gln Leu Val Val Glu Pro Glu Gly
                245                 250                 255

Gly Ala Val Ala Pro Gly Gly Thr Val Thr Leu Thr Cys Glu Ala Pro
            260                 265                 270

Ala Gln Pro Pro Pro Gln Ile His Trp Ile Lys Asp Gly Arg Pro Leu
        275                 280                 285

Pro Leu Pro Pro Gly Pro Met Leu Leu Leu Pro Glu Val Gly Pro Glu
    290                 295                 300

Asp Gln Gly Thr Tyr Ser Cys Val Ala Thr His Pro Ser His Gly Pro
```

```
            305                 310                 315                 320
Gln Glu Ser Arg Ala Val Ser Val Thr Ile Ile Glu Thr Gly Glu Glu
                325                 330                 335
Gly Thr Thr Ala Gly Ser Val Glu Gly Pro Gly Leu Glu Thr Leu Ala
            340                 345                 350
Leu Thr Leu Gly Ile Leu Gly Gly Leu Gly Thr Val Ala Leu Leu Ile
            355                 360                 365
Gly Val Ile Val Trp His Arg Arg Gln Arg Lys Gly Gln Glu Arg
        370                 375                 380
Lys Val Pro Glu Asn Gln Glu Glu Glu Glu Arg Ala Glu Leu
385                 390                 395                 400
Asn Gln Pro Glu Glu Pro Glu Ala Ala Glu Ser Ser Thr Gly Gly Pro
                405                 410                 415

<210> SEQ ID NO 3
<211> LENGTH: 1405
<212> TYPE: DNA
<213> ORGANISM: Human

<400> SEQUENCE: 3 gggggcagccg gaacagcagt tggagcctgg gtgctggtcc tcagtctgtg gggggcagta      60
gtaggtgctc aaaacatcac agcccggatt ggcgagccac tggtgctgaa gtgtaagggg     120
gccccccaaga aaccacccca gcggctggaa tggaaactga acacaggccg acagaagct     180
tggaaggtcc tgtctcccca gggaggaggc cctgggaca gtgtggctcg tgtccttccc      240
aacggctccc tcttccttcc ggctgtcggg atccaggatg aggggatttt ccggtgcagg     300
gcaatgaaca ggaatggaaa ggagaccaag tccaactacc gagtccgtgt ctaccagatt     360
cctgggaagc cagaaattgt agattctgcc tctgaactca cggctggtgt tcccaataag     420
gtggggacat gtgtgtcaga gggaagctac cctgcaggga ctcttagctg gcacttggat     480
gggaagcccc tggtgcctaa tgagaaggga gtatctgtga aggaacagac caggagacac     540
cctgagacag gctcttcac actgcagtcg gagctaatgg tgaccccagc ccggggagga     600
gatccccgtc ccaccttctc ctgtagcttc agcccaggcc ttccccgaca ccgggccttg     660
cgcacagccc ccatccagcc ccgtgtctgg gagcctgtgc ctctggagga ggtccaattg     720
ggtggtggag ccagaaggtg gagcagtagc tcctggtgga accgtaaccc tgacctgtga     780
agtccctgcc cagccctctc ctcaaatcca ctggatgaag gatggtgtgc cctgccccttt    840
ccccccagcc ctgtgctgat cctccctgag atagggcctc aggaccaggg aacctacagc     900
tgtgtggcca cccattccag ccacgggccc caggaaagcc gtgctgtcag catcagcatc     960
atcgaaccag cgcgaggaggg gccaactgca ggctctgtgg gaggatcagg ctgggaact    1020
ctagccctgg ccctggggat cctgggaggc ctggggacag ccgccctgct cattgggggtc   1080
atcttgtggc aaaggcggca acgccgagga gaggagagga ggcccagaa aaccaggagg    1140
aagaggagga gcgtgcagaa ctgaatcagt cggaggaacc tgaggcaggc gagagtacta   1200
ctggagggcc ttgagggggcc cacagacaga tcccatccat cagctcccctt ttcttttttcc  1260
cttgaactgt tctggcctca gaccaactct ctcctgtata atctctctcc tgtataacccc    1320
caccttgcca gctttcttc tacaaccaga gccccccaca atgatgatta aacacctgac     1380
acatctttgc aaaaaaaaaa aaaaa                                          1405

<210> SEQ ID NO 4
<211> LENGTH: 405
```

-continued

```
<212> TYPE: PRT
<213> ORGANISM: Human

<400> SEQUENCE: 4

Gly Ala Ala Gly Thr Ala Val Gly Ala Trp Val Leu Val Leu Ser Leu
  1               5                  10                  15

Trp Gly Ala Val Val Gly Ala Gln Asn Ile Thr Ala Arg Ile Gly Glu
             20                  25                  30

Pro Leu Val Leu Lys Cys Lys Gly Ala Pro Lys Lys Pro Pro Gln Arg
         35                  40                  45

Leu Glu Trp Lys Leu Asn Thr Gly Arg Thr Glu Ala Trp Lys Val Leu
     50                  55                  60

Ser Pro Gln Gly Gly Pro Trp Asp Ser Val Ala Arg Val Leu Pro
 65                  70                  75                  80

Asn Gly Ser Leu Phe Leu Pro Ala Val Gly Ile Gln Asp Glu Gly Ile
                 85                  90                  95

Phe Arg Cys Arg Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
        195                 200                 205

Ser Phe Ser Pro Gly Leu Pro Arg His Arg Ala Leu Arg Thr Ala Pro
    210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
                245                 250                 255

Leu Thr Cys Glu Val Pro Ala Gln Pro Ser Pro Gln Ile His Trp Met
            260                 265                 270

Lys Asp Gly Val Pro Leu Pro Leu Pro Pro Ser Pro Val Leu Ile Leu
        275                 280                 285

Pro Glu Ile Gly Pro Gln Asp Gln Gly Thr Tyr Ser Cys Val Ala Thr
    290                 295                 300

His Ser Ser His Gly Pro Gln Glu Ser Arg Ala Val Val Ser Ile Ser
305                 310                 315                 320

Ile Ile Glu Pro Gly Glu Gly Pro Thr Ala Gly Ser Val Gly Gly
                325                 330                 335

Ser Gly Leu Gly Thr Leu Ala Leu Ala Leu Gly Ile Leu Gly Gly Leu
            340                 345                 350

Gly Thr Ala Ala Leu Leu Ile Gly Val Ile Leu Trp Gln Arg Arg Gln
        355                 360                 365

Arg Arg Gly Glu Glu Arg Lys Ala Pro Glu Asn Gln Glu Glu Glu Glu
    370                 375                 380
```

```
-continued

Glu Arg Ala Glu Leu Asn Gln Ser Glu Glu Pro Glu Ala Gly Glu Ser
385                 390                 395                 400

Ser Thr Gly Gly Pro
            405
```